United States Patent [19]

Van Tonder

[11] Patent Number: 5,194,264
[45] Date of Patent: Mar. 16, 1993

[54] PESTICIDAL FORMULATION

[75] Inventor: Stephanus J. Van Tonder, Johannesburg, South Africa

[73] Assignee: Scientific Chemicals (Proprietary) Limited, Johannesburg, South Africa

[21] Appl. No.: 492,791

[22] Filed: Mar. 13, 1990

[30] Foreign Application Priority Data

| Mar. 13, 1989 | [ZA] | South Africa | 89/1896 |
| Mar. 13, 1989 | [ZA] | South Africa | 89/1897 |
| Aug. 18, 1989 | [ZA] | South Africa | 89/6323 |

[51] Int. Cl.$^5$ .............................................. A01N 25/00
[52] U.S. Cl. .................................. 424/405; 424/400; 424/45
[58] Field of Search .................... 514/67; 424/405

[56] References Cited

U.S. PATENT DOCUMENTS

| 4,668,666 | 5/1987 | Allan et al. | 514/67 |
| 4,731,378 | 3/1988 | Naik et al. | 31/215 |
| 4,764,529 | 8/1988 | Naik et al. | 31/215 |
| 4,822,614 | 4/1989 | Rodeno | 424/405 |
| 4,853,223 | 8/1989 | Graf | 424/405 |
| 4,888,274 | 12/1989 | Farquharson | 424/405 |
| 4,888,325 | 12/1989 | Schroeder | 424/405 |

FOREIGN PATENT DOCUMENTS

| 581404 | 2/1989 | Australia | 25/16 |
| 1142850 | 3/1983 | Canada | 167/4.1 |
| 1252040 | 4/1989 | Canada | 167/18.8 |
| WO8607525 | 12/1986 | PCT Int'l Appl. | 25/2 |
| 827614 | 10/1982 | South Africa . | |
| 1580251 | 2/1977 | United Kingdom . | |
| 2052259 | 5/1980 | United Kingdom . | |

*Primary Examiner*—Thurman K. Page
*Assistant Examiner*—William E. Benston, Jr.
*Attorney, Agent, or Firm*—Gifford, Groh, Sprinkle, Patmore & Anderson

[57] ABSTRACT

A pesticidal formulation for external application comprises at least one pesticide effective against ectoparasites and at least one polar solvent for the pesticide. The pesticide and solvent together constitute a pesticidal component comprising a solution of the pesticide in the solvent. The pesticidal component is admixed with an aqueous component. The pesticidal component is miscible in the aqueous component. Water constitutes at least 30% m/v of the formulation. No solvent having a solubility in water of 15 gm/l or less at ambient temperature, is present.

9 Claims, No Drawings

PESTICIDAL FORMULATION

THIS INVENTION relates to a pesticidal formulation. It relates also to a method of making a pesticidal formulation.

According to a first aspect of the invention, there is provided a method of making a pesticidal formulation for external application, which comprises dissolving a pesticide effective against ectoparasites in a polar solvent, to form a pesticidal component comprising a solution of the pesticide in the solvent; and admixing the pesticidal component with an aqueous component to form a pesticidal formulation, in which the pesticidal component is miscible in the aqueous component, with the provisos that water constitutes at least 30% m/v of the pesticidal formulation and that no solvent having a solubility in water of 15 gm/l or less at ambient temperature, is present.

The aqueous component may comprise water and a surfactant, and the pesticidal component a synthetic pyrethroid. The method may include adding to the pesticidal component a synergist for the synthetic pyrethroid.

According to a second aspect of the invention, there is provided a pesticidal formulation for external application, which comprises at least one pesticide effective against ectoparasites;

at least one polar solvent for the pesticide, so that the pesticide and solvent together constitute a pesticidal component comprising a solution of the pesticide in the solvent; and an aqueous component with which the pesticidal component is admixed, with the pesticidal component being miscible in the aqueous component, with the provisos that water constitutes at least 30% m/v of the formulation and that no solvent having a solubility in water of 15 gm/l or less at ambient temperature, is present.

The pesticide of the present formulation is hence effective against ectoparasites such as ticks and fleas, and active ingredients or pesticides effective specifically against endoparasites such as helminths, ie anthelmintics, are hence excluded.

The aqueous component may comprise an admixture of water and a surfactant, with the pesticide comprising at least one of a synthetic pyrethroid, an amidine, chlormethiuron, cyromazine, and s-methoprene.

The synthetic pyrethroid, when present, may be selected from the group comprising alphamethrin, allethrin, barthrin, bioresmethrin, biopermethrin, cismethrin, cyclethrin, cypermethrin, cyhalothrin, cyfluthrin, cyphenothrin, deltamethrin, dimethrin, fenpropanate, fenvalerate, flumethrin, fluvalinate, indothrin, permethrin, phenothrin, phthalthrin, pyrethrum, resmethrin, tetramethrin, sumithrin, tralomethrin and tralocythrin.

The amidine, when present, may be selected from the group comprising chlordimeform, clenpyrin, cymiazole and amitraz.

The formulation may also include a surfactant or emulsifier component in admixture with the water.

When the pesticide is, or includes, a synthetic pyrethroid, the formulation may also include a synergist for the pyrethroid, ie a substance capable of enhancing its efficacy and/or spectrum or range of activity. The synergist may then be selected from the group comprising piperonyl butoxide, bucarpolate, N-octyl bicyclohexene dicarboximide, 1,2-methylendioxy-4-(2-(octylsulfinyl)-propyl)-benzol, propylisome, propinylcarbamate, propihylether, propinyloxime, propinylphosphonate, sesamex, S,S,S-tributylphosphorothioate and sulfoxide.

The solvent will thus be selected such that the pesticide is soluble therein, and the proportion of pesticide to solvent will thus naturally be such that the pesticide does not exceed its solubility limit in the solvent at room temperature. The solvent will also be selected such that it, and more particularly, the pesticidal component formed when the pesticide is dissolved therein, is miscible in water, or more particularly, in the aqueous component comprising water and the surfactant. The proportion or ratio of the pesticidal component to the aqueous component will thus naturally be such that the miscibility limit of the pesticidal component in the aqueous component is not exceeded.

Generally, the polar solvent has a solubility in water at ambient temperature (20°-25° C.) of at least 20 gm/l, and generally as high as 400-500 gm/l or even more. The solvent can be selected from the group comprising alcohols, eg methanol, ethanol, isopropanol, n-butanol; ketones, eg acetone, methyl ethyl ketone, diethylketone; lactones, eg gamma buteryl lactone; ketoalcohols, eg diacetone alcohol; glycols, eg ethylene glycol, propylene glycol, hexylene glycol, glycerine; glycolethers, eg triethyleneglycol, dipropyleneglycol, tripropyleneglycol, polyethyleneglycol 200, diethylglycol-monoethyl-ether (Carbitol, Ethyldiglycol), dipropyleneglycol-mono-methyl-ether, triethylene-mono-methyl-ether; alkanolamines, eg mono-,di,triethanolamine; sulfoxides, eg dimethylsulfoxide; pyrolidones, eg n-methylpyrolidone or pyrolidone; or even other suitable aprotic solvents such as dimethyl or diethyl formamide. For example, the solvent may be diacetone alcohol, which is miscible with water in all proportions and in which synthetic pyrethroids and amidines are generally and readily soluble. The formulation is characterized thereby that it does not include a solvent having a solubility in water of 15 mg/l or less, eg non-polar solvents, such as a petroleum distallate or dibutyl phthalate.

The surfactant may comprise an anionic surfactant and/or a cationic surfactant and/or a non-ionic surfactant. The anionic surfactant, when present, may be selected from the group comprising fatty acid sulphates; fatty acid ether sulphonates and their salts; alkyl aryl sulphonates, such as the sulphonate of dodecyl benzene, and their salts; fatty acid salts; mono-,di-,tri-aryl polyglycolether phosphoric acid esters and their salts. The cationic surfactant, when present, may be a quaternary ammonium salt or a phenyl derivative thereof. The non-ionic surfactant, when present, may be selected from the group comprising polyethoxylated castor oil, sorbitan, sorbitan esters, fatty alcohols, acids and esters, alkylphenols such as ethoxylated nonyl phenol, block polymers of ethylene and propylene oxide and their alkyl, aryl or alkylaryl condensates.

Generally, when more than one pesticide is present, the mass ratio of the one pesticide to the other may be between 1:10 and 10:1, eg between 1:1.5 and 10:5. The mass ratio of pesticide to synergist, when present, may be between 1:10 and 10:1, eg between 1:3 and 10:5.

Typically, the mass proportion of pesticide to solvent can be between 1:5 and 1:15, eg about 1:10, while the mass proportion of pesticidal component to water can be between 0.01:100 and 1:10.

The formulation may comprise (all percentages hereinafter are given in 'm/v' unless otherwise indicated, where 'm/v' means grams of a particular component in 100 ml of formulation)

| | |
|---|---|
| pesticide | 0.001–30.000% |
| synergist | 0.001–30.000% |
| surfactant | 0.050–50.000% |
| solvent | 0.050–49.000% |
| water | balance to make up 100%, but being between 31.000 and 99.990% |

In one embodiment of the invention, the formulation can be suitable for use as a pour-on formulation, ie for application topically in localized fashion to an animal to be treated, eg along the animal's back. The formulation may then comprise, when the pesticide is, or includes, a synthetic pyrethroid,

| | |
|---|---|
| synthetic pyrethroid as pesticide | 1–3% |
| synergist | 5–15% |
| surfactant | 5–40% |
| polar solvent for the pesticide | 10–49% |
| water | balance to make up 100% but being at least 31% |

When the pesticide is not a synthetic pyrethroid, the formulation may then comprise

| | |
|---|---|
| pesticide | 0.15–3% |
| surfactant | 5.0–40% |
| polar solvent for the pesticide | 10.0–49% |
| water | balance to make up 100% but being at least 31% |

More particularly, the pour-on formulation may comprise cypermethrin as synthetic pyrethroid

| | |
|---|---|
| pesticide | 2.0% |
| piperonyl butoxide as synergist for the pesticide | 10.0% |
| nonylphenylethoxylate as surfactant | 25.0% |
| diacetone alcohol as polar solvent for the pesticide | 20.0% |
| water | 45.3% |

In another embodiment of the invention, the formulation can be suitable for use as a spray when diluted with water. The formulation may then comprise, when the pesticide is, or includes, a synthetic pyrethroid, and is intended for use on animals

| | |
|---|---|
| synthetic pyrethroid as pesticide | 0.125–2.52% |
| synergist | 0.625–12.6% |
| surfactant | 5.0–20.0% |
| polar solvent for the pesticide | 30.0–49.0% |
| water | balance to make up 100% but being at least 31% |

When the pesticide is not a synthetic pyrethroid, the formulation may then comprise

| | |
|---|---|
| pesticide | 0.15–3.0% |
| surfactant | 5.0–20.0% |
| polar solvent for the pesticide | 2.0–49.0% |
| water | balance to make up 100% but being at least 31% |

When the water-dilutable spray formulation is intended for use on other substrates such as plants, and the pesticide is, or includes, a synthetic pyrethroid, the formulation may comprise

| | |
|---|---|
| synthetic pyrethroid as pesticide | 0.02–10.0% |
| synergist | 0.10–30.0% |
| surfactant | 2.0–20.0% |
| polar solvent for the pesticide | 5.0–49.0% |
| water | balance to make up 100% but being at least 31% |

When the pesticide is not a synthetic pyrethroid, the formulation may comprise

| | |
|---|---|
| pesticide | 0.02–10.0% |
| surfactant | 2.0–20.0% |
| polar solvent for the pesticide | 5.0–49.0% |
| water | balance to make up 100% but being at least 31% |

More particularly, the sprayable composition may then comprise

| | |
|---|---|
| cypermethrin as synthetic pyrethroid pesticide | 0.8% |
| piperonyl butoxide as synergist for the pesticide | 4.0% |
| nonylphenolethoxylate as surfactant | 0.5% |
| ethoxylated castor oil as a further surfactant | 5.0% |
| diacetone alcohol as polar solvent for the pesticide | 5.0% |
| water | 85.2% |

The garden spray formulation may also include a fungicide component. The formulation may then comprise, when the pesticide is, or includes, a synthetic pyrethroid

| | |
|---|---|
| synthetic pyrethroid as pesticide | 0.02–10.0% |
| synergist | 0.10–30.0% |
| surfactant | 2.0–20.0% |
| polar solvent for the pesticide | 5.0–49.0% |
| fungicide component | 0.01–10.5% |
| water | balance to make up 100% but being at least 31% |

When the pesticide is not a synthetic pyrethroid, the formulation may then comprise

| | |
|---|---|
| pesticide | 0.02–10.0% |
| surfactant | 2.0–20.0% |
| polar solvent for the pesticide | 5.0–49.0% |
| fungicide component | 0.01–10.5% |
| water | balance to make up 100% but being at least 31% |

The fungicide component may comprise one or more of benconazole, benlate, or etaconazole. The fungicide component may hence comprise, in respect of the formulation

| | |
|---|---|
| penconazole | 0.01–0.5% |
| benlate | 0.25–10.0% |

In yet another embodiment of the invention, the formulation can be suitable for use as an animal dip when diluted with water. The formulation may then comprise, when the pesticide is, or includes, a synthetic pyrethroid,

| | |
|---|---|
| synthetic pyrethroid | 0.001–2.52% |
| synergist | 0.005–12.6% |
| surfactant | 0.100–30.0% |
| polar solvent for the insecticide | 1.0–49.0% |
| water | balance to make up 100% but being at least 31% |

The formulation may then, when the pesticide is not a synthetic pyrethroid, comprise

| | |
|---|---|
| pesticide | 0.15–3.0% |
| surfactant | 0.10–30.0% |
| polar solvent for the insecticide | 1.0–49.0% |
| water | balance to make up 100% but being at least 31% |

More particularly, the formulation may then comprise cypermethrin as synthetic pyrethroid

| | |
|---|---|
| pesticide | 0.25% |
| cymiazole as amidine pesticide | 0.30% |
| piperonyl butoxide as synergist for the cypermethrin | 1.25% |
| nonylphenylethoxylate as surfactant | 20.00% |
| diacetone alcohol as solvent | 47.00% |
| water | 31.30% |

In yet another embodiment of the invention, the formulation may be suitable for use as a directly applied tickicidal composition, and may then comprise, when the pesticide is, or includes, a synthetic pyrethroid,

| | |
|---|---|
| synthetic pyrethroid as pesticide | 0.001–3.0% |
| synergist | 0.005–15.0% |
| surfactant | 0.050–1.0% |
| polar solvent | 0.080–5.0% |
| water | balance to make up 100% but being at least 31% |

When the pesticide is not a synthetic pyrethroid, the formulation may then comprise

| | |
|---|---|
| pesticide | 0.001–3.0% |
| surfactant | 0.050–1.0% |
| polar solvent | 0.080–5.0% |
| water | balance to make up 100% but being at least 31% |

More particularly, the formation may then comprise cypermethrin as synthetic pyrethroid

| | |
|---|---|
| pesticide | 0.0025% |
| piperonyl butoxide as synergist for the pesticide | 0.0125% |
| nonylphenylethoxylate as surfactant | 0.0500% |
| diacetone alcohol as polar solvent for the pesticide | 0.0800% |
| water | 99.8% |

If desired, components such as a conditioning agent, a bacteriostat such as formalin, colouring agent, and a perfume can be added to the compositions, with a corresponding water reduction then taking place.

According to a third aspect of the invention, there is provided a pesticidal formulation for external application, which comprises
at least one pesticide effective against ectoparasites;
a shampoo base; and
an aqueous component as carrier for the pesticide and the shampoo base, with the proviso that the formulation does not contain a solvent having a solubility in water of 15 gm/l or less at ambient temperature.

The pesticide and aqueous component may be as hereinbefore described, while the shampoo base may be, or include, a surfactant as hereinbefore described. The shampoo formulation can be used at a rate of 2-10 ml/kg animal body mass.

The pesticidal formulation in accordance with the third aspect of the invention may comprise, when the pesticide is, or includes, a synthetic pyrethroid,

| | |
|---|---|
| synthetic pyrethroid as pesticide | 0.0312–0.63% |
| synergist | 0.156–3.15% |
| surfactant | 5.0–20.0% |
| shampoo base | 2.8–22.4% |
| water | balance to make up 100% but being at least 31% |

When the pesticide is not a synthetic pyrethroid, the formulation may then comprise

| | |
|---|---|
| pesticide | 0.0375–0.75% |
| surfactant | 5.0–20.4% |
| shampoo base | 2.8–22.4% |
| water | balance to make up 100% but at least 31% |

More particularly, the formulation may then comprise cypermethrin as synthetic pyrethroid

| | |
|---|---|
| pesticide | 0.06% |
| piperonyl butoxide as synergist for the pesticide | 0.30% |
| nonylphenylethoxylate as surfactant | 10.00% |
| sodium-laurylethersulphonate as the shampoo base, as a 28% concentration in water | 60.00% (16.8% shampoo base) |
| water | 74.0% |

The formulations may be for use on animals such as cattle, sheep, dogs, cats, pigs, horses, and the like. The pesticide, solvent and surfactant will hence be selected to be compatible with the animal on which the formulation is intended for use. The animals may be treated every 1 to 2 weeks, for effective control of ectoparasites such as ticks, fleas, lice, flies, fungi, acarids, insects, and the like.

The invention will now be described by way of example with reference to the following non-limiting examples.

EXAMPLE 1

A pour-on formulation in accordance with the invention and having the following composition, was made up:

| | |
|---|---|
| cypermethrin | 2% |
| piperonyl butoxide | 10% |
| nonylphenylethoxylate | 25% |
| diacetone alcohol | 20% |
| water | 45.3% |

The formulation was made up by initially admixing the cypermethrin, piperonyl butoxide and diacetone alcohol to form a pesticidal composition in which the cypermethrin and piperonyl butoxide were dissolved in the diacetone alcohol. To the pesticidal formulation was added the nonylphenylethoxylate, and thereafter the water. The pesticidal component was wholly miscible in the water so that the resultant formulation was in the form of a solution containing substantially no suspended solids and not being in the form of an emulsion. There was no separation out of the different phases after allowing the formulation to stand for a prolonged period of time. The pour-on formulation is suitable for irradicating or combatting ectoparasites such as ticks and fleas on ruminants, such as cattle, when applied as a pour-on. It can be applied at a dosage of between 5 ml/100 kg body mass and 100 ml/100 kg animal body mass along the animal's back every 7 days to 2 weeks, depending on parasite challenge. It can also be used in a prophylactic manner by applying it at said dosage at said intervals for prevent said pests from becoming established on the animals. Furthermore, at the proportions as given, the pesticide is believed to function substantially non-systemically.

The formulation of Example 1 was used for the in-vitro determination of LC-50 values, as compared to a commercially available dip containing 14% cypermethrin in the form of an emulsifiable concentrate. The method used was the standard Larval Packet Test as described by SABS ('South African Bureau of Standards') Method No. 1094. Two tick strains were used, namely *Boophilus decoloratus* and *Amblyomma hybraeum*.

In addition, the in-vivo acaricidal efficacy for the pour-on formulation of Example 1 was determined. The cattle used were crossbred steers subjected to natural tick infestation in a natural environment. Tick strains identified were *Amblyomma hebraeum*, *Boophilus decoloratus* and *Rhipicephalus appendiculatus*. Treatment of the cattle involved pouring the product along the backline of the steer at a dosage volume of 10ml/100kg body mass. Cattle were treated on days 0, 7 and 14, and the results are set out in Graph 3.

Still further, in-vivo fly repellency assessment of the pour-on formulation of Example 1, was also carried out. The cattle used were Bonsmara cows subjected to natural fly infestation in a natural environment. The fly strains identified were face flies, which are the most difficult to treat as they do not normally settle on the host. The same method as used for the in-vivo acaricidal efficacy determination described hereinbefore, was used. The results are set out in Graph 4, and it will be noted that the cows were treated on days 5/2 and 20/2.

EXAMPLE 2

A formulation, suitable for use as a garden spray, was made up in similar fashion to the formulation of Example 1, and comprised the following:

| | |
|---|---|
| cypermethrin | 0.8% |
| piperonyl butoxide | 4% |
| nonylphenylethoxylate | 0.5% |
| ethoxylated castor oil | 5% |
| diacetone alcohol | 5% |
| water | 85.3% |

This formulation can be used as a garden spray by diluting 5ml thereof in one liter of water prior to use.

This garden spray formulation was tested for insecticidal efficacy on the following garden and crop pests: aphids, ants, astylus beetle, bollworm, caterpillars, crickets, cutworm, fleas, harvester termites, moth larvae, plusia loopers, thrips and white fly.

In all cases, the total percentage of pests killed compared to untreated control groups exceeded 99%.

EXAMPLE 3

A formulation in accorance with the invention, and suitable for use as a dip, was made up by admixing, in a similar fashion to that described in Example 1, the following components:

| | |
|---|---|
| cypermethrin | 0.25% |
| cymiazole | 0.30% |
| piperonyl butoxide | 1.25% |
| nonylphenylethoxylate | 20% |
| diacetone alcohol | 47% |
| water | 31.2% |

This dip was used, by diluting one part by volume thereof, with 100 parts by volume of water, to assess its efficacy in control of ticks and fleas on dogs. The dogs utilized for the test consisted of a group of nine dogs of a cross-section of small to large and a mixture of short and long haircoat. A similar group of six dogs was used as control. All dogs were subjected to natural tick and flea infestations in a natural environment. Each of the treated dogs was dipped by complete immersion. The dogs were dipped on days 0 and 7.

EXAMPLE 4

A formulation in accordance with the invention, and suitable for use as a pesticidal shampoo, was made up by admixing the following components:

| | |
|---|---|
| cypermethrin | 0.06% |
| piperonyl butoxide | 0.3% |
| nonylphenylethoxylate | 10% |
| sodium laurylethersulphonate, as a 28% concentration in water | 60% |
| water | 74% |

This shampoo formulation was tested to assess its efficacy in the control of ticks and fleas on dogs. Two groups of dogs, as hereinbefore described with reference to Example 3, were again tested. The treated group of dogs were shampood with the equivalent of 10ml/kg body mass of the shampoo formulation, rinsed and allowed to dry naturally.

EXAMPLE 5

A formulation in accordance with the invention and suitable as a ready-to-use directly applicable composition, eg for the spot-treatment of ticks, was made up by admixing the following constituents in a similar manner as described for Example 1:

| | |
|---|---|
| cypermethrin | 0.0025% |
| piperonyl butoxice | 0.0125% |
| nonylphenylethoxylate | 0.05% |
| diacetone alcohol | 0.08% |
| water | 99.8% |

This formulation was tested to assess its efficacy in controlling Rhioiceohalus evertsi on horses. The formulation was sprayed directly on the infested areas of the horses in the treated group, which were kept separate from a control group of horses.

EXAMPLE 6

A pour-on formulation can be made up in the same fashion as described in Example but using any of the other synthetic pyrethroids hereinbefore described apart from cypermethrin.

EXAMPLE 7

A pour-on formulation can be made up by admixing the following in a similar fashion to that described in Example 1:

| | |
|---|---|
| chlordimeform, clenpyrin, cymiazole, amitraz*, chlormethiuron, cyromazine or s-methoprene, as pesticide | 2% |
| nonylphenylethoxylate | 25% |
| diacetone alcohol | 20% |
| water | 54% |

*In this, and subsequent examples, stabilized amitraz is used.

EXAMPLE 8

A formulation suitable as a garden spray can be made up in a similar fashion to that described in Example 2, with the following constituents:

| | |
|---|---|
| chlordimeform, clenpyrin, cymiazole, amitraz, chlormethiuron, cyromazine or s-methoprene, as pesticide | 0.8% |
| nonylphenylethoxylate | 0.5% |
| ethoxylated castor oil | 5% |
| diacetone alcohol | 5% |
| water | 88.8% |

EXAMPLE 9

A formulation in accordance with the invention and suitable for use as a dip, can be made up in a similar fashion to that described in Example using the following constituents:

| | |
|---|---|
| chlordimeform, clenpyrin, cymiaxole, chlormethiuton, cyromazine, or s-methoprene as pesticide | 0.3% |
| nonylphenylethoxylate | 20% |
| diacetone alcohol | 47% |
| water | 31.8% |

EXAMPLE 10

A pesticidal shampoo formulation in accordance with the invention can be made up, in a similar fashion to the procedure described in Example 4, with the following components:

| | |
|---|---|
| chlordimeform, clenpyrin, cymiazole, amitraz, chlormethiuron, cyromazine or s-methoprene, as pesticide | 0.06% |
| nonylphenylethoxylate | 10% |
| sodium laurylethersulphonate, as a 28% concentration in water | 60% |
| water | 73.8% |

EXAMPLE 11

A directly applicable pesticidal formulation in accordance with the invention can be made up by admixing the following components, in a similar fashion to the procedure described in Example 1:

| | |
|---|---|
| chlordimeform, clenpyrin, cymiazole, amitraz, chlormethiuron, cyromazine or s-methoprene, as pesticide | 0.0025% |
| nonylphenylethoxylate | 0.05% |
| diacetone alcohol | 0.08% |
| water | 99.8% |

EXAMPLE 12

A pesticidal formulation in accordance with the invention suitable, after dilution with water, as a garden spray, can be made up by following the procedure set out in Example 1, and using the following components:

| | |
|---|---|
| cypermethrin | 0.8% |
| piperonyl butoxide | 4% |
| nonylphenylethoxylate | 0.5% |
| ethoxylated castor oil | 5% |
| diacetone alcohol | 5% |
| penconazole and/or etaconazole and/or benlate as fungicide component | 1% |
| water | 85% |

EXAMPLE 13

A pour-on formulation in accordance with the invention and having the following composition, can be made up using the procedure of Example 1:

| | |
|---|---|
| as synthetic pyrethroid, allethrin, deltamethrin, fenvalerate, fluvalerate or sumithrin | 2% |
| piperonyl butoxide | 10% |
| ethoxylated castor oil as surfactant | 25% |
| as polar solvent, propylene glycol methyl ether, n-methylpyrolidone, gamma buteryl lactone, or dipropylene glycol methyl ether | 20% |
| water | balance to make up 100% |

EXAMPLE 14

A pour-on formulation in accordance with the invention and having the following composition, can be made up using the procedure of Example 1:

| | |
|---|---|
| as pesticide, chlordimeform, clenpyrin, cymiazole, amitraz, chlormethiuron, cyromazine or s-methoprene | 2% |
| epoxidized castor oil as surfactant | 25% |
| as solvent, propylene glycol methyl ether, n-methylpyrolidone, gamma buteryl lactone, or dipropylene glycol methyl ether | 20% |
| water | balance to make up 100% |

EXAMPLE 15

A garden spray formulation in accordance with the invention, and having the following composition can be made up using the procedure of Example 1:

| | |
|---|---|
| cypermethrin | 0.2% |
| cyromazine | 2.0% |
| piperonyl butoxide | 1.0% |
| ethoxylated castor oil | 25% |
| methyoxy propanol | 20% |
| water | 52.3% |

FURTHER EXAMPLES

Formulations similar to those of Examples 2 to 12 can be made up, using the procedure of Example 1, but substituting the following:
- where cypermethrin is used, substituting it with allethrin, deltamethrin, fenvalerate, fluvalerate or sumithrin
- where diacetone alcohol is used, substituting it with propylene glycol methyl ether, n-methylpyrolidone, gamma buteryl lactone, or dipropylene glycol methyl ether The Applicant believes that, with the hydrotropic carrier system employed in the formulations according to the invention, pesticides which can normally not be used in pure solvent based formulations, eg pure solvent based pour-on formulations, for example due to their skin irritancy, can now be used since, amongst other, the water provides a satisfactory dilution medium for diluting the pesticide down to non-irritancy levels on application. In the case of pour-on formulations, the use of water as carrier also results in a pour-on formulation having good spreadability over the entire pelt or skin of the animal, and low skin penetration.

However, to safeguard further against possible skin irritancy, a refatting agent which replenishes skin fat, can be included in the formulation. When present, the refatting agent can be present in an amount of about 3%, with the corresponding reduction in the volume of water. The skin refattiong agent can be isopropyl myristate.

Further advantages of the pesticidal formulations in accordance with the invention are
- the formulations have high pesticidal activity, but low mammalian and bird toxicity since no non-polar or petroleum distillate type solvent is used
- the formulations can have very low negative environmental impact, depending on the specific constituents or components used
- when formulated for use on plants, the components can be selected so as to prevent or minimize phytotoxicity
- risk of skin damage and irritation when applied to animals is reduced or eliminated as a result of the high proportion of water present in the formulations
- good pesticidal efficacy is obtainable since the high proportion of water, which ensures good spreadability, will result in the pesticide being spread more evenly and effectively on the animal or plant
- the formulation can, in certain instances, have components which enhance wetting and spreading characteristics on the target pest, thereby ensuring rapid penetration of the pesticide into the target pest
- due to the relatively low proportions of active ingredients and solvents, formulations are cost-effective, eg cheaper than pure solvent based systems
- the formulations are safe to handle
- the formulations are generally poorly flammable or non-flammable, and therefore safer to handle and transport
- the formulations can, in certain instances, be made up to be completely biodegradable

I claim:

1. A method of making a pesticidal formulation for external application with the following percentages of ingredients, which comprises
   dissolving 0.001–30.000% of a pesticide and mixtures thereof selected from the group consisting of a synthetic pyrethroid, an amidine, chlormethiuron, cyromazine, and s-methoprene, effective against ectoparasites in a polar solvent of 0.050–49.000% selected from the group consisting of alcohols, ketones, lactones, keto-alcohols, glycols, glycolethers, amides, alkanolamines, sulfoxides and pyrolidones, to form a pesticidal component comprising a solution of the pesticide in said polar solvent; and
   admixing the pesticidal components with an aqueous component of 31.000–99.990% to form a pesticidal formulation, in which the pesticidal component is wholly miscible in the aqueous component, with the formulation being in the form of a solution containing substantially no suspended solids and not being in the form of an emulsion, with the provisos that water constitutes at least 30% m/v of the pesticidal formulation and that no solvent having a solubility in water of 15 gm/l or less at ambient temperature, is present.

2. A method according to claim 1, wherein the aqueous component comprises water and a surfactant, and the pesticidal component a synthetic pyrethroid, with the method including adding to the pesticidal component a synergist for the synthetic pyrethroid in a proportion of 0.050–49.00% with the water being present in the proportion of 31.000–99.990% and the surfactant in a proportion of 0.050–50.000% with the synergist being selected from the group consisting in piperonyl butoxide, bucarpolate, N-octyl bicyclohexane dicarboximide, 1,2-methylendioxy-4-(2-(octyl-sulfinyl)-propyl)-benzol, propylisome, propinylcarbamate, propinylether, propinyloxime, propinylphosphonate, sesamex, s,s,s,-tributylphosphorothicate and sulfoxide.

3. A pesticidal formulation with the following percentages of ingredients for external application which comprises at least one pesticide selected from the group consisting of a synthetic pyrethroid, an amidine, chlormethiuron, cyromazine, a s-methoprene, effective against ectoparasites, in a proportion of 0.001–30.000% based on the total formulation;

at least one polar solvent for the pesticide, so that the pesticide and solvent together constitute a pesticidal component comprising a solution of the pesticide in the solvent with the polar solvent of 0.050–49.000% selected from the group consisting of alcohols, ketones, lactones, keto-alcohols, glycols, glycolethers, amides, alkanolamines, sulfoxides and pyrolidones; and an aqueous component with which the pesticidal component is admixed, with the pesticidal component being miscible in the aqueous component so that the formulation is in the form of a solution containing substantially no suspended solids and not being in the form of an emulsion, with the provisos that water constitutes at least 30% m/v of the formulation and that no solvent having a solubility in water of 15 gm/l or less at ambient temperature, is present, and with the aqueous component being present in a proportion of 31.000–99.990%.

4. A pesticidal formulation according to claim 3, wherein the aqueous component comprises an admixture of water and a surfactant, with the pesticide comprising at least one synthetic pyrethroid, and a synergist, in the proportion of 0.001–30.000% for said one synthetic pyrethroid with the water being present in the proportion of 31.000–99.990% and the surfactant in a proportion of 0.050–50.000% and the synergist being selected from the group consisting of piperonyl butoxide, bucarpolate, N-octyl bicylohexane dicarboximide, 1,2-methylendioxy-4-(2-(octyl-sulfinyl)-propyl)-benzol, propylisome, propinycarbamate, propinylether, propinyloxime, propinylphosphonate, sesamex, S,S,S-tributylphosphorothioate and sulfoxide.

5. A pesticidal formulation according to claim 3 which comprises

| cypermethrin as synthetic pyrethroid pesticide | 0.25% |
| cymiazole as amidine pesticide | 0.30% |
| piperonyl butoxide as synergist for the cypermethrin | 1.25% |
| nonylphenylethoxylate as surfactant | 20.00% |
| diacetone alcohol as solvent | 47.00% |
| water | 31.3% |

6. A pesticidal formulation for external application, which comprises cypermethrin as a synthetic pyrethroid pesticide effective against ectoparasites —0.25% cymiazole as an amidine pesticide effective against ectoparasites —0.30% piperonyl butoxide as a synergist for the cypermethrin —1.25% diacetone alcohol as a polar solvent for the cypermethrin, cymiazole and piperonal butoxide, and with these components together constituting a pesticidal component comprising a solution of the cypermethrin, cymiazole and piperonul butoxide in the diacetone alcohol —47.00% nonylphenylethoxylate as a surfactant —20.00% water, with the water and surfactant constituting an aqueous component with which the pestidical component is admixed and with which the pesticidal component is miscible, the water thus constituting at least 30% m/v of the formulation —31.3%.

7. A pesticidal formulation according to claim 3 which comprises

| cypermethrin as synthetic pyrethroid pesticide | 0.001–2.52% |
| cymiazole as amidine pesticide | 0.001–2.52% |
| piperonyl butoxide as synergist | 0.005–12.6% |
| nonylphenylethoxylae as surfactant | 0.100–30.0% |
| diacetone alcohol as solvent | 1.0–49.0% |
| water | balance to make up 100% |

8. A pesticidal formulation for external application, which comprises at least one pesticide selected from the group consisting of a synthetic pyrethroid, an amidine, chlormethiuron, cyromazine and s-methoprene —0.001–30.0% at least one polar solvent selected from the group consisting of alcohols, ketones, lactones, keto-alcohols, glycols, glycoethers, amides, alkanolamines, sulfoxides and pyrolidones —0.05–49.0% a surfactant selected from the group consisting in fatty acid sulphates, fatty acid ether sulphonates and their salts, alkyl aryl sulphonates and their salts, fatty acid salts, mono,-di-,tri-aryl polyglycolether phosphoric acid esters and their salts, a quaternary ammonium salt or a phenyl derivative thereof, polyethoxylated castor oil, sorbitan, sorbintan esters, fatty alcohols, fatty acids, fatty esters, alkylphenols, block polymers of ethylene and propylene oxie and their alkyl, aryl and alkylaryl condensates —0.100–50.0% water, with the water and the surfactant constituting an aqueous component with which the pesticidal component is admixed, with the pesticidal component being miscible in the aqueous component so that the formulation is in the form of a solution containing substantially no suspended solids and not being in the form of an emulsion, and with the proviso that no solvent having solubility in water of 15 gm/l or less at ambient termperature is present —31.000–99.000%.

9. A pesticidal formulation according to claim 8, wherein said at least one pesticide is at least one synthetic pyrethroid effective against ectoparasites and selected from the group consisting of alphametherin, allethrin, barthrin, bioresmethrin, biopermethrin, cismethrin, cyclethrin, cypermethrin, cyhalothrin, cyfluthrin, cyphenothrin, deltamethrin, dimethrin, fenpropanate, fenvalerate, flumethrin, fluvalinate, indothrin, permethrin, phenothrin, phthalthrin, pyrethrum, resmethrin, tetramethrin, sumithrin, tralomethrin and tralocythin —0.001–2.52% a synergist for the synthetic pyrethroid and selected from the group consisting of piperonyl butoxide, bucarpolate, N-octyl bicylohexane dicarboximide, 1,2-methylendioxy-4-(2-(octyl-sulfinyl)-propyl)-benzol, propylisome, propinylcarbamate, propinylether, propinyloxime, propinylphosphonate sesamex, S,S,S-tributylphosphorothioate and sulfoxide —0.05–12.6%
said polar solvent being selected for said synthetic pyrethroid and said synergists, so that the synthetic pyrethoid, synergist and solvent together constitute a pesticidal component comprising a solution of the synthetic pyrethroid and synergist in the solvent, with the polar solvent being selected from the group consisting of keto-alcohols, lactones, alkonalamines and pyrolidones — 1.0–49.0%
said surfactant being —0.100–30.0%.

* * * * *